United States Patent
Chang et al.

(10) Patent No.: US 11,408,015 B2
(45) Date of Patent: Aug. 9, 2022

(54) EXPRESSION VECTOR, RECOMBINANT MICROORGANISM AND METHOD FOR PRODUCING 1,5-DIAMINOPENTANE

(71) Applicant: China Petrochemical Development Corporation, Taipei (Taiwan), Kaohsiung (TW)

(72) Inventors: Jo-Shu Chang, Kaohsiung (TW); I-Son Ng, Kaohsiung (TW); Shih-Fang Huang, Kaohsiung (TW); Hong-Yi Lin, Kaohsiung (TW); Sheng-Feng Li, Kaohsiung (TW); Chia-Wei Tsai, Kaohsiung (TW); Chih-Yu Huang, Kaohsiung (TW); Wan-Wen Ting, Kaohsiung (TW)

(73) Assignee: China Petrochemical Development Corporation, Kaohsiung (TW)

( * ) Notice: Subject to any disclaimer, the term of this patent is extended or adjusted under 35 U.S.C. 154(b) by 0 days.

(21) Appl. No.: 17/062,783

(22) Filed: Oct. 5, 2020

(65) Prior Publication Data
US 2021/0317483 A1 Oct. 14, 2021

(30) Foreign Application Priority Data
Apr. 14, 2020 (TW) ................. 109112489

(51) Int. Cl.
*C12P 13/00* (2006.01)
*C12N 1/20* (2006.01)
*C12R 1/19* (2006.01)

(52) U.S. Cl.
CPC ............ *C12P 13/001* (2013.01); *C12N 1/205* (2021.05); *C12R 2001/19* (2021.05)

(58) Field of Classification Search
None
See application file for complete search history.

(56) References Cited

U.S. PATENT DOCUMENTS

2006/0160191 A1* 7/2006 Kataoka ................. C12N 15/70
435/106

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AEJ10559. Sep. 21, 2006 (Year: 2006).*
Zhou et al. Microb Cell Fact. 2017; 16: 84. Published online May 16, 2017 (Year: 2017).*

* cited by examiner

*Primary Examiner* — Christian L Fronda
(74) *Attorney, Agent, or Firm* — McCarter & English, LLP; Yu Lu

(57) ABSTRACT

Provided is an expression vector including a nucleotide sequence for encoding lysine decarboxylase CadA, and a sequence of a constitutive promoter for regulating the expression of the nucleotide sequence. Also provided is a recombinant microorganism including the expression vector and a method of producing 1,5-diaminopentane by using the recombinant microorganism.

11 Claims, 9 Drawing Sheets

Specification includes a Sequence Listing.

EXPRESSION VECTOR, RECOMBINANT MICROORGANISM AND METHOD FOR PRODUCING 1,5-DIAMINOPENTANE

CROSS-REFERENCE TO RELATED APPLICATION

This application claims foreign priority under 35 U.S.C. § 119(a) to Patent Application No, 109112489 filed on Apr. 14, 2020, in the Intellectual Property Office of Ministry of Economic Affairs, Republic of China (Taiwan, R.O.C.), the entire content of which is incorporated herein by reference.

REFERENCE TO SEQUENCE LISTING

This application contains a Sequence Listing in computer readable form, which has been submitted electronically via EFS-web in ASCII format. Said ASCII copy, created on Oct. 2, 2020, is named Seq_Listing_123710_06401 and is 15,334 bytes in size. The computer readable form of the sequence listing is part of the specification or is otherwise incorporated herein by reference.

BACKGROUND

1. Technical Field

The present disclosure relates to a microorganism for producing 1,5-diaminopentane, and in particular to a recombinant microorganism and a method for producing 1,5-diaminopentane.

2. Description of the Related Art 1,5-diaminopentane is an important monomer for the synthesis of polymers such as polyamide (i.e., nylon). The existing methods for producing 1,5-diaminopentane by microorganisms can be roughly divided into three types: (1) the method of microbial metabolism in vivo; (2) the co-culture method, in which two microorganisms are co-cultured, and the product of one of the two microorganisms is used as a substrate for the other microorganism; and (3) whole-cell bioconversion in vitro, in which a whole biological organism is uses as a catalyst for chemical conversion; that is, the microorganism is cultured to a certain cell amount, and then a substrate is added for catalysis and conversion to a product.

Microorganisms that can be used to produce 1,5-diaminopentane include Escherichia coli (E. coli), which can express lysine decarboxylase, CadA, and catalyze the conversion of lysine to produce diaminopentane. Studies on the production of diaminopentane through the microbial metabolism include: the method comprising using glucose as a carbon source, and after removing the genes for product metabolism, expressing CadA by a low copy number vector p15A containing Tac promoter, in which the highest yield is only 9.6 g/L [1]; and the method comprising using galactose as a carbon source and expressing CadA by a high copy number vector pETDuet, in which the highest yield is only 8.8 g/L [2]. From the above two examples, the high-yield diaminopentane cannot be obtained by regulating the metabolic pathway of E. coli. The possible reason is that since the cells produce substrates and products at the same time, it leads to a slow production rate of the products.

In 2018, Wang et al. used co-culture to generate substrates and products by individual strains, and the two strains used different carbon sources (the former used glucose, while the latter used glycerol). Without competing with each other, the final yield can reach 28.5 g/L after 50 hours of fermentation [3]. The co-culture method can indeed increase yield; in terms of time efficiency, however, the yield is still unsatisfactory.

The whole-cell bioconversion approach provides an alternative solution, which comprises increasing the amount of bacteria and accumulating the amount of enzymes through high-density fermentation, and then catalyzing the conversion of lysine to 1,5-diaminopentane (DAP, also known as cadaverine). In 2014, Weichao Ma et al. used the pETDuet expression system to simultaneously express CadA and cadaverine/lysine antiporter (CadB). After catalysis with cells in an amount of 8 g/L for 16 hours, the maximum yield can reach 221 g/L [4]. In addition, in 2015, Kim et al. used pET24m to express CadA. As a result, the enzyme activity was 30.27 mmol/cell dry weight (mg)/min, and after 2 hours of catalysis, the final yield was 142.8 g/L [5].

Moreover, CN Patent Publication No. 105316270 discloses that the CadA gene and the CadB gene containing $RBS_{22}$ are inserted into the pET28a (+) vector, and an E. coli strain B is used as a host. CN Patent Publication No. 104498519 also discloses that pETDuet is used as a vector to express CadA and CadB, wherein 5' end of CadB is fused with a periplasmic pectate lyase (pelB) leader sequence. Furthermore, EP Patent Publication No. 1482055 discloses that CadA is constructed into pUC18 vector, and an E. coli strain K-12 JM109 is used as a host.

However, the existing whole-cell bioconversion for producing 1,5-diaminopentane, including the above-mentioned methods of whole-cell bioconversion, mostly employ the E. coli T7 expression system, which must be added with expensive inducers such as isopropyl β-d-1-thiogalactopyranoside (IPTG) for culture. Also, since the induction time and the required concentration of the inducer need to be precisely controlled, it is very unfavorable for the production of whole-cell enzymes in high quantities. In addition, since E. coli BL21 (DE3) as a host in the T7 system has poor tolerance to its own product, i.e., 1,5-diaminopentane, the production of 1,5-diaminopentane is thus limited as well.

In view of the foregoing, it is necessary to provide a method that can effectively increase the production capacity of 1,5-diaminopentane to solve the existing problems in the conventional technology.

SUMMARY OF THE DISCLOSURE

In order to solve the above-mentioned problems, the present disclosure provides an expression vector, comprising a nucleotide sequence for encoding lysine decarboxylase CadA and a sequence of a constitutive promoter for regulating expression of the nucleotide sequence.

In an embodiment, the nucleotide sequence for encoding lysine decarboxylase CadA is a sequence having at least 80% identity to SEQ ID NO: 1 and having the same activity as SEQ ID NO: 1. For example, the nucleotide sequence encodes a protein having lysine decarboxylase activity. In another embodiment, the lysine decarboxylase CadA has an amino acid sequence of SEQ ID NO: 2 or an amino acid sequence of SEQ ID NO: 2 with a conservative substitution.

In an embodiment, the constitutive promoter is one of J series constitutive promoters. In another embodiment, the J series constitutive promoters include promoters J23100, J23101, J23102, J23103, J23104, J23105, J23106, J23107, J23108, J23109, J23110, J23111, J23112, J23113, J23114, J23115, J23116, J23117, J23118 and J23119. In yet another embodiment, the constitutive promoter is J23100, J23109 or J23114.

In an embodiment, the constitutive promoter has a sequence having at least 80% identity to SEQ ID NO: 3 and has the same activity as SEQ ID NO: 3. For example, the constitutive promoter has a sequence that is capable of being a constitutive promoter.

In an embodiment, the expression vector has a sequence having at least 80% identity to SEQ ID NO: 4 and has the same activity as SEQ ID NO: 4.

The present disclosure also provides a recombinant microorganism comprising the expression vector as described above, which may be used to produce 1,5-diaminopentane.

In an embodiment, the microorganism is genus *Escherichia, Klebsiella, Erwinia, Serratia, Providence, Corynebacterium* or *Brevibacterium*. In another embodiment, the microorganism is *Escherichia coli*. In yet another embodiment, the microorganism is *E. coli* strain K-12 W3110. In an embodiment, the recombinant microorganism provided by the present disclosure is *Escherichia coli* W3110-JcadA, which is a strain deposited at Bioresource Collection and Research Center (BCRC) of the Food Industry Research and Development Institute under BCRC Accession No. BCRC 940690 on Dec. 19, 2019, and also deposited at Leibniz Institute DSMZ-German Collection of Microorganisms and Cell Cultures under DSMZ Accession No. DSMZ 33576 on Jul. 15, 2020.

The present disclosure also provides a method for producing 1,5-diaminopentane, comprising: mixing the above-mentioned microorganism with lysine in a solution to convert the lysine to 1,5-diaminopentane; and recovering the 1,5-diaminopentane from the solution.

In an embodiment, the method further comprises culturing the above-mentioned microorganism in a medium. In another embodiment, the culture of the microorganism is performed by high-density fermentation. In yet another embodiment, the culture of the microorganism is performed before the microorganism and lysine are mixed in the solution.

In an embodiment, the concentration of the microorganism mixed with lysine in the solution is 1 to 6 of an optical density measured at a wavelength of 600 nm ($OD_{600}$). In another embodiment, the concentration of the lysine in the solution is 1 M to 2 M. In yet another embodiment, the concentration of the lysine in the solution is 1 M, 1.2 M, 1.4 M, 1.5 M, 1.6 M, 1.8 M or 2 M.

In an embodiment, the solution has a pH value of 4 to 8. In another embodiment, the pH value of the solution is 4, 4.5, 5, 5.5, 6, 6.5, 6.8, 7, 7.5 or 8.

In an embodiment, the method further comprises adding a cofactor to the solution, wherein the concentration of the cofactor in the solution is 0.01 mM to 0.05 mM. In another embodiment, the concentration of the cofactor in the solution is 0.01 mM, 0.02 mM, 0.03 mM, 0.04 mM, or 0.05 mM. In yet another embodiment, the cofactor is pyridoxal-5'-phosphate (PLP).

The present disclosure utilizes a non-inducible expression system to express lysine decarboxylase CadA in a microbial host as a whole-cell biocatalyst, which provides, e.g., high protein expression, high enzyme activity and slow degradation rate, such that the catalytic efficiency of diaminopentane of microorganisms may be significantly improved. In addition, the whole-cell biocatalyst is capable to produce 1,5-diaminopentane without an additional inducer, and thus the cost of producing 1,5-diaminopentane is reduced and the production process is simplified, thereby enhancing the production capacity and yield of diaminopentane, and realizing the large-scale production of 1,5-diaminopentane.

DETAILED DESCRIPTION OF THE EMBODIMENTS

Figure 1A:
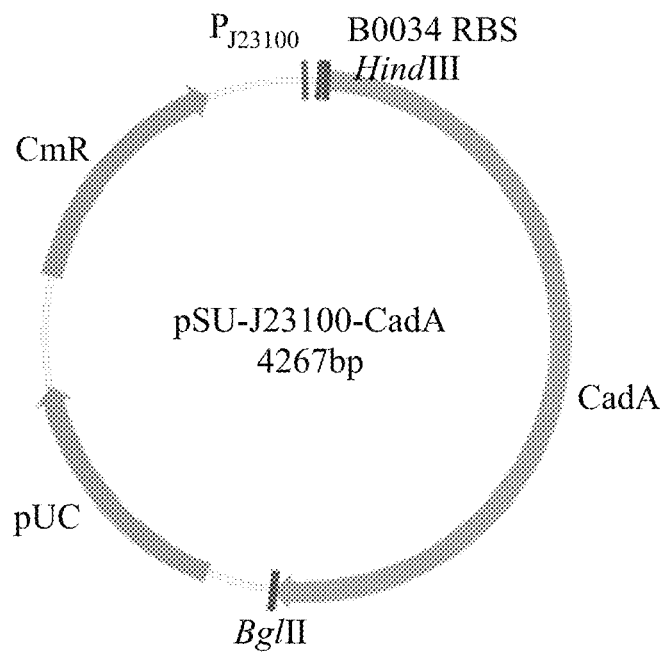
FIG. 1A is a schematic diagram of the gene map of constitutive expression plasmid pSU-J23100-CadA. $P_{J23100}$: J23100 promoter; B0034 RBS: ribosome binding site; CadA: lysine decarboxylase CadA gene; pUC: origin of replication of plasmid pSU; CmR: chloramphenicol acetyltransferase gene; HindIII and BglII: restriction sites.

The detailed description of the present disclosure is described by the embodiments below. Those skilled in the art can easily understand the advantages and effects of the present disclosure from the contents disclosed in this specification. The present disclosure can also be implemented or applied by other different embodiments. The details in this specification can also be modified and changed based on different viewpoints and applications, without departing from the scope of the present disclosure. In addition, all ranges and numerical values herein are inclusive and combinable. Any value or point that falls within the range described herein, such as any integer, can be used as the minimum or maximum value to derive the subordinate range.

Unless otherwise stated in the text, the singular forms "a," "an" and "the" used in the specification and the appended claims include plural individuals.

Unless otherwise stated in the text, the term "or" used in the scope of the specification and the attached claims includes the meaning of "and/or."

The present disclosure provides an expression vector, which includes a nucleotide sequence for encoding lysine decarboxylase CadA and a sequence of a constitutive promoter for regulating expression of the nucleic acid molecule encoding the lysine decarboxylase. The present disclosure also provides a recombinant microorganism containing the expression vector and a method for producing 1,5-diaminopentane using the microorganism.

As used herein, the term "lysine decarboxylase" refers to an enzyme that participates in the biotechnological production of 1,5-diaminopentane in an organism, including two types of lysine decarboxylase, i.e., lysine decarboxylase 1 (CadA) and lysine decarboxylase 2 (LdcC). CadA is an inducible enzyme that may be induced by oxygen starvation, excessive lysine supply, and pH changes, whereas LdcC is a constitutive enzyme, which is independent of an external change in pH [6].

According to one embodiment of the present disclosure, the nucleotide sequence for encoding lysine decarboxylase CadA is a sequence having at least 80% (e.g., at least 82%, at least 85%, at least 90%, at least 95%, at least 98%, or at least 100%) identity to SEQ ID NO: 1, and having the same activity as SEQ ID NO: 1, such as a sequence that may encode a protein having lysine decarboxylase activity. In another embodiment, the lysine decarboxylase CadA has an amino acid sequence of SEQ ID NO: 2 or an amino acid sequence of SEQ ID NO: 2 with a conservative substitution.

As used herein, the term "sequence identity percentage" means the extent that amino acid or nucleotide residues of a candidate protein or nucleic acid fragment are identical to amino acid or nucleotide residues of a reference protein or nucleic acid fragment. When performing the above-mentioned comparison, the candidate protein or nucleic acid fragment and the reference protein or nucleic acid fragment are aligned, and gaps may be introduced as necessary, so as to form the highest sequence identity between the two sequences. When calculating the identity, the amino acid residue where is conservative substitution is regarded as different residue; the nucleotide residues which are degenerate codons are also regarded as different residues. For example, as to the codons AAU and AAC that both encode aspartic acid, it is considered that there is a different residue U or C between such two codons.

It should be understood that, compared to the amino acid or nucleotide sequence of the reference protein or nucleic acid fragment in the present disclosure, amino acid or nucleotide sequence of candidate protein or nucleic acid fragment with a modification (e.g., deletion, substitution, or addition) in at least a portion of the sequence is also within the scope of the present disclosure, as long as the resulting candidate protein or nucleic acid fragment has substantially the same biological activity as the amino acid or nucleotide of the reference protein or nucleic acid fragment. This results from the codon degeneracy. For example, in the nucleotide sequence for encoding CadA of the present disclosure, various modifications can be made in the coding region, provided that it does not change the activity of the polypeptide expressed from the coding region. Therefore, the nucleotide sequence for encoding CadA of the present disclosure may be a nucleotide sequence having SEQ ID NO: 1 or any nucleotide sequence having at least 80% identity to SEQ ID NO: 1, as long as the protein encoded by the nucleotide sequence exhibits CadA activity. For the same reasons, CadA of the present disclosure may have the amino acid sequence of SEQ ID NO: 2 or be a protein that is homologous to SEQ ID NO: 2, as long as the protein substantially exhibits CadA activity.

As used herein, the term "constitutive promoter" refers to a promoter that maintains constitutive activity in most of or in all tissues. Compared with an inducible promoter, which must be regulated by external signals or inducers, the constitutive promoter can continuously express a specific gene.

The suitable constitutive promoters for the present disclosure include those belonging to the J series constitutive promoters, for example, J23100, J23101, J23102, J23103, J23104, J23105, J23106, J23107, J23108, J23109, J23110, J23111, J23112, J23113, J23114, J23115, J23116, J23117, J23118 and J23119. In an embodiment, the constitutive promoter used in the present disclosure may be J23100, J23109 or J23114. In another embodiment, the constitutive promoter has the sequence of SEQ ID NO: 3 or at least 80% (e.g., at least 82%, at least 85%, at least 90%, at least 95%, at least 98% or at least 100%) identity to SEQ ID NO: 3, and has the same activity as SEQ ID NO: 3; for example, the constitutive promoter has a sequence that can be used as a constitutive promoter.

According to one embodiment of the present disclosure, the expression vector of the present disclosure further includes at least one selected from the group consisting of a marker gene sequence, a reporter gene sequence, an antibiotic resistance gene sequence, a restriction enzyme cleavage position sequence, a polyadenylation position sequence, an enhancer subsequence, a terminal subsequence and a regulator subsequence. In another embodiment, the expression vector has the sequence of SEQ ID NO: 4 or a sequence having at least 80% (e.g., at least 82%, at least 85%, at least 90%, at least 95%, at least 98% or at least 100%) identity to SEQ ID NO: 4 and having the same activity as SEQ ID NO: 4.

As used herein, the term "recombination" refers to artificially combining two separate sequence fragments. In general, the term "recombination" refers to a nucleic acid, a protein or a microorganism containing genetic materials derived from multiple different sources, or being encoded by genetic materials derived from multiple different sources, such as two or more organisms of different strains or species.

As used herein, the term "microorganism" refers to microscopic organism, including bacteria, archaea, viruses, or fungi. As used herein, the term "microorganism" should be interpreted to encompass the "bacteria."

Microbial hosts suitable for the expression vector of the present disclosure include, but are not limited to, microorganisms being genus *Escherichia, Klebsiella, Erwinia, Serratia, Providencia, Corynebacterium* or *Brevibacterium*. In an embodiment, the microbial host used in the present disclosure can express the lysine decarboxylase CadA in vivo. In another embodiment, the microbial host used in the present disclosure not only expresses the lysine decarboxylase CadA in vivo, but also has tolerance to diaminopentane.

According to one embodiment of the present disclosure, the method for producing 1,5-diaminopentane of the present disclosure includes culturing the above-mentioned microbial host in a medium under a condition sufficient to produce lysine decarboxylase CadA. In an embodiment, the medium may be LB medium. In another embodiment, the method includes culturing the microorganism by high-density fermentation.

According to one embodiment of the present disclosure, the method further includes adjusting the concentration of the cultured microorganism to $OD_{600}$ 1 to 6, and then mixing the microorganism with lysine in a solution.

According to one embodiment of the present disclosure, the lysine concentration in the solution is 1 M to 2 M. According to another embodiment of the present disclosure, the pH value of the solution may be 4 to 8.

According to one embodiment of the present disclosure, the solution may further contain a cofactor at a concentration of 0.01 mM to 0.05 mM.

As used herein, the term "cofactor" includes a non-protein compound that is required for an enzyme to be catalytically active. The compound may be organic or inorganic. For example, the cofactors suitable for the present disclosure include, but are not limited to, pyridoxal-5'-phosphate (PLP).

Many examples have been used to illustrate the present disclosure. The examples below should not be taken as a limit to the scope of the present disclosure.

EXAMPLES

Materials:

Sodium chloride was purchased from Sigma Aldrich Co. (USA). Yeast extract was purchased from Oxoid (Taiwan). Trypsin was purchased from Cyrusbioscience (Taiwan). Agar was purchased from BD Difco dehydration medium (France). Agarose was purchased from GeneDireX (Taiwan). Pyridoxal-5'-phosphate (PLP), diethyl ethoxymethylenemalonate (DEEMM) and sodium acetate were purchased from Sigma Aldrich Co. (USA). L-lysine hydrochloride was purchased from Cyrusbioscience (Taiwan). D(+)-glucose was purchased from Comieco (Italy). Potassium dihydrogen phosphate and dipotassium hydrogen phosphate were purchased from Showa Chemical Industry Co. (Japan). Acetonitrile used for HPLC analysis was purchased from Spectrum Chemical Manufacturing Corp. (USA). The PCR reagent Ex-Taq was purchased from Takara Bio Inc. (USA). Restriction enzymes were purchased from New England Biolabs (USA). T4 DNA ligase was purchased from Leadgene Co., Ltd. (Korea). The primers were synthesized by Integrated DNA Technologies (USA).

Example 1: Construction of Recombinant Expression Vector

With using the genome of *E. coli* K-12 MG1655 as a template, primers HindIII-CadA-F (5'-GCA AGC TTA TGA ACG TTA TTG CAA TAT TGA ATC AC-3' (SEQ ID NO: 5)) and BglII-CadA-R (5'-GCA GAT CTT CAT TTT TTG CTT TCT TTC AAT ACC TTA ACG GTA TAG CGG CC-3' (SEQ ID NO: 6)) were synthesized for polymerase chain reaction (PCR).

The PCR was used to amplify specific DNA sequence fragments. The required materials included DNA template, 5'-end primer, 3'-end primer, deoxynucleotide triphosphate (dNTP), 10× polymerase buffer, and polymerase. The polymerase used in this example included Ex-Taq. The PCR product was analyzed by DNA electrophoresis and recovered by tapping, so as to obtain the amplified lysine decarboxylase CadA fragment.

The amplified CadA fragment was digested with HindIII and BglII, and then the CadA fragment was inserted into the pSU-J23100 vector to construct plasmid pSU-J23100-CadA. As shown in FIG. 1A, the plasmid contains a constitutive promoter J23100 (Accession No.: LP934757), a ribosome binding site B0034RBS (Biobrick No. BBa B0034), and CadA gene regulated by the promoter J23100.

For transformation, commercially available DH5a competent cells were added with about 10 μL of plasmid pSU-J23100-CadA. The mixture was left on ice for 30 minutes, further put in a water bath at 42° C. for 1.5 minutes, and then put on ice for 10 minutes. Next, after adding 400 μL of LB liquid medium or SOC (super optimal broth with catabolites repression) medium, the mixture was shaken in an incubator at 37° C. for about 60 to 90 minutes, and then was subject to centrifuge at 4000 rpm for 3 minutes. After removing 300 μL of supernatant, all competent cells containing recombinant DNA were coated on solid medium containing antibiotics, and cultured overnight at 37° C.

Figure 1B:
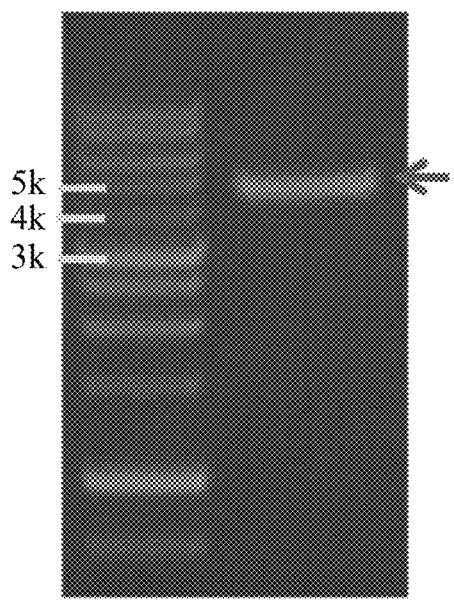
FIG. 1B shows the result of DNA electrophoresis of the plasmid pSU-J23100-CadA, indicating that the plasmid has a total length of about 4000 base pairs (bp), which is consistent with that shown in FIG. 1A. Molecular weight markers 3k, 4k, and 5k represent 3000, 4000, and 5000 bp, respectively.

Several colonies generated on this solid medium were selected and inoculated into liquid medium in a test tube containing antibiotics, and cultured overnight in an incubator at 37° C. The next day, 2 mL of bacterial solution was taken from the medium for plasmid extraction. The extracted plasmids were then verified by restriction enzyme cleavage. The plasmid pSU-J23100-CadA had a total length of 4267 bp, which was consistent with the DNA electrophoresis result shown in FIG. 1B (i.e., the fragment indicated by the arrow), implying that the CadA gene was successfully constructed in pSU vector.

Example 2: Expression Host Test

In order to select microorganisms with better tolerance to diaminopentane as the expression host, three common *E. coli* strains were selected: BL21, K-12 W3110 and MG1655.

Figure 2:
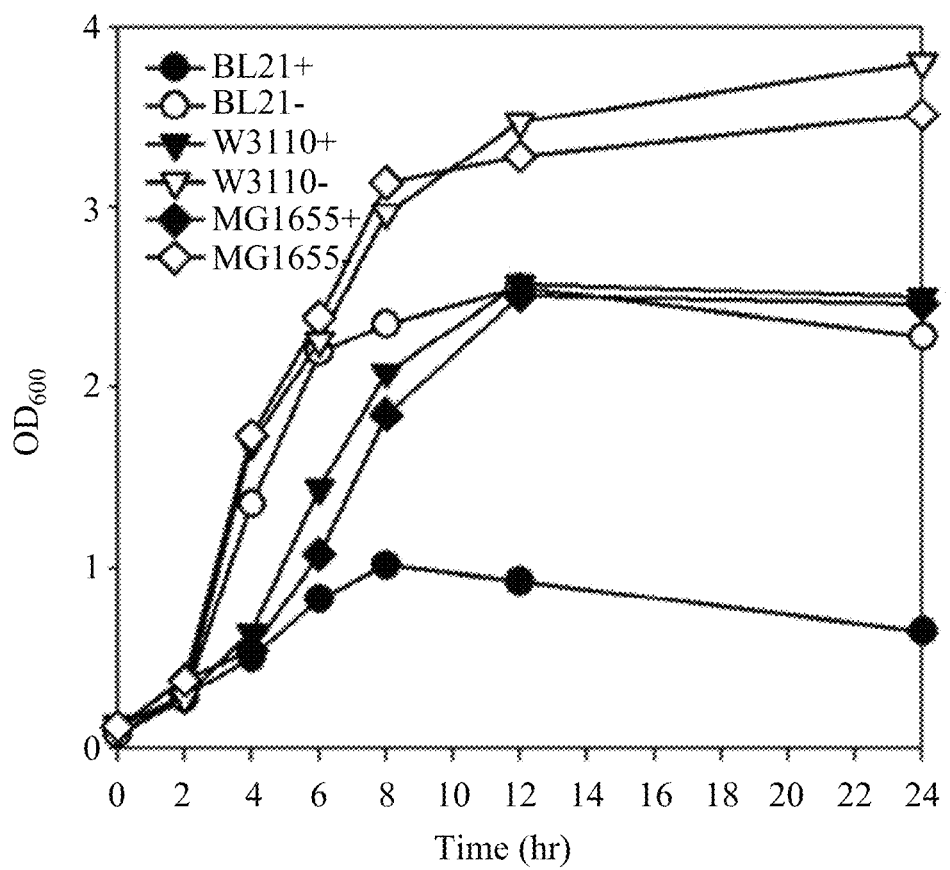
FIG. 2 shows the tolerance of three *E. coli* strains to diaminopentane. BL21, W3110, MG1655: three *E. coli* strains BL21, K12 W3110 and MG1655; "+": the medium containing diaminopentane; "−": the medium not containing diaminopentane.

First, the three strains were individually cultured for 2 hours, and then 0.2 M of diaminopentane was added to the medium of the three strains. As shown in FIG. 2, without the addition of diaminopentane, W3110 and MG1655 grew faster than BL21; while after the addition of diaminopentane, the growth rates of the three strains were all delayed, and the bacterial numbers were all decreased. However, W3110 has the fastest growth rate and the least decrease in the period of 4 to 12 hours, and thus was considered as having higher tolerance to pentadiamine. Therefore, *E. coli* strain K-12 W3110 was subsequently selected as the expression host.

Example 3: Preparation of Recombinant Microorganisms

The plasmid pSU-J23100-CadA prepared in Example 1 and stored in the selected host *E. coli* DH5a was subjected to plasmid extraction and transformed into *E. coli* strain K-12 W3110. The protein expression was analyzed after 12 hours of culture, in which wild-type W3110 was taken as a control.

Figure 3:
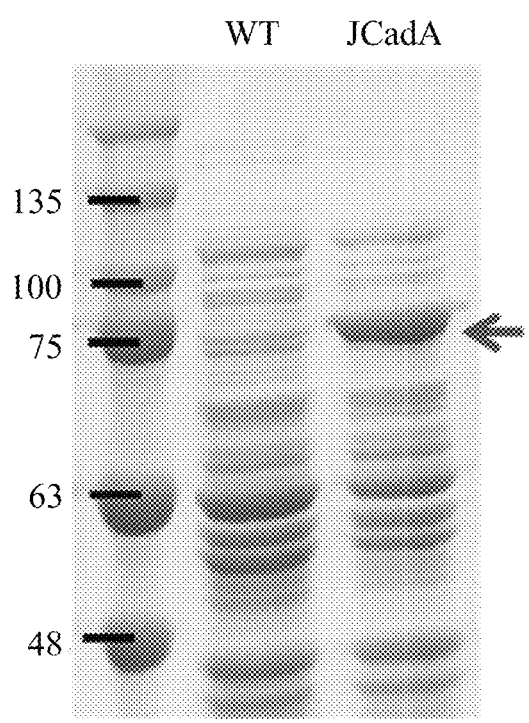
FIG. 3 shows the protein expression of the transformed strains after culture for 12 hours. WT: wild type W3110; JCadA: transformed strain JCadA/W3110. The unit of molecular weight marker is kDa.

As shown in FIG. 3, the transformed strain JCadA (hereinafter also referred to as JCadA/W3110 or W3110-JCadA) has a higher CadA expression level (i.e., the fragment indicated by the arrow) than the wild-type W3110 (WT).

The *E. coli* transformed strain W3110-JCadA has been deposited under Budapest Treaty at Leibniz Institute DSMZ-German Collection of Microorganisms and Cell Cultures (Inhoffenstr. 7 B, D-38124 Braunschweig, Germany) on Jul. 15, 2020 and has been given the DSMZ Accession No. DSM 33576 by the International Depositary Authority. This biological material was subjected to the viability test and passed.

Example 4: Activity Test of Recombinant Microorganisms

The transgenic strain JCadA/W3110 of Example 3 was cultured and then centrifuged at 10,000 rpm for 10 minutes. The cell pellet was then suspended in deionized water, and the optical density of the bacterial solution at 600 nm wavelength ($OD_{600}$) was adjusted to reach 6 ($OD_{600}$=6). Next, the mixture was added in a solution containing 1 M of lysine as a substrate and 0.05 mM of pyridoxal-5'-phosphate (PLP) as a cofactor, and placed in an incubator with oscillation for reaction (35° C., 200 rpm). During the reaction, the contents of the remaining lysine and diaminopentane produced in the solution were confirmed.

Figure 4:
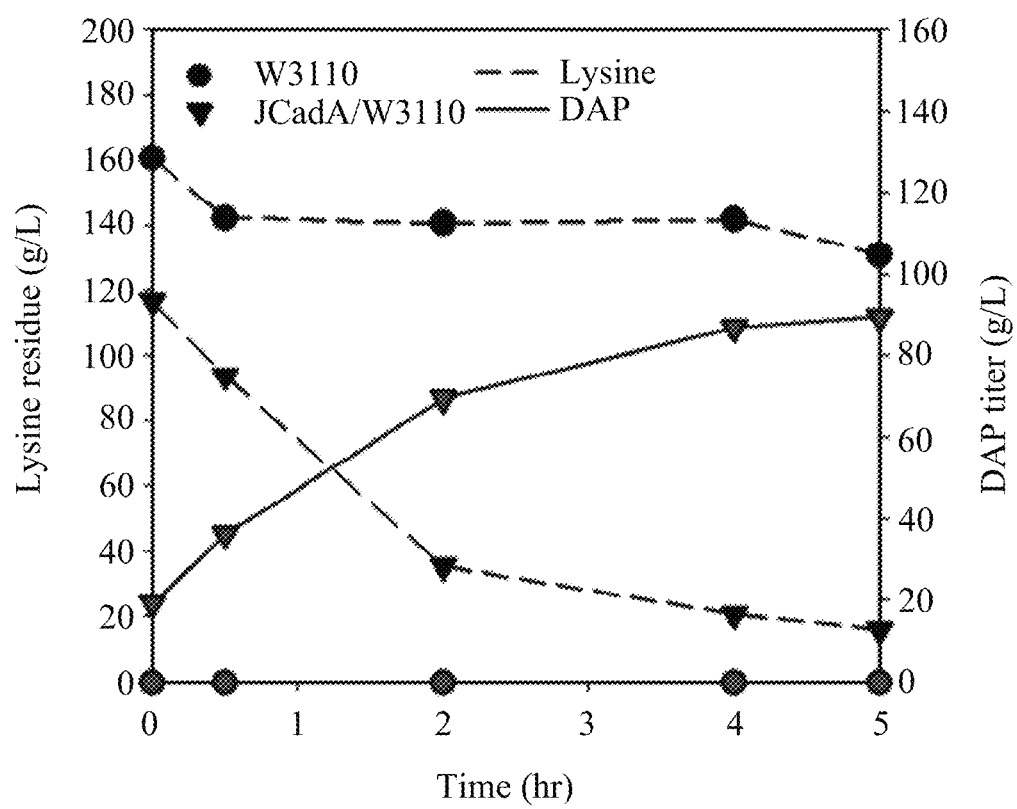
FIG. 4 shows the results of whole-cell catalytic production of the transformed strain JCadA/W3110. Hour 0 is the starting point for adding 1 M substrate (i.e., lysine) and 0.05 mM cofactor (i.e., PLP). W3110: wild type W3110.

As shown in FIG. 4, by using the transgenic strain JCadA/W3110 as a whole-cell biocatalyst, as the catalytic reaction time increases, the content of lysine decreases, and the content of diaminopentane increases, indicating that the transformed strain JCadA/W3110 can catalyze the bioconversion of lysine to diaminopentane. In contrast to the wild-type W3110, the residual amount of lysine was only slightly reduced, and no diaminopentane was produced. It can be seen that a whole-cell biocatalyst using the constitutive expression system indeed exhibits more CadA activity than the wild-type W3110, and can quickly catalyze the production of 1,5-diaminopentane in vitro.

Example 5: Comparison of Yield and Activity of Inducible and Constitutive Microbial Systems In order to compare the CadA activity of the strains with the constitutive expression system and the inducible expression system, JCadA/W3110 (constitutive strain) and T7cadA/BL21 (DE3) (inducible strain) were individually cultured in LB medium in 5 L fermentation tanks (FB-6S, FIRSTEK, Taiwan) under the same conditions, and the bacterial growth number and activity within 33 hours of culture were recorded. The conditions of the fermentation tank were as follows: dissolved oxygen (DO) 10 to 30%, air flow rate 1.5 vvm, pH=6.8, 32° C., and 100 rpm. IPTG inducer was additionally added to the medium of T7cadA/BL21 (DE3) in a concentration of 0.00167 g/L. The number of bacteria was represented by the OD value which was measured with a spectrophotometer at a wavelength of 600 nm, and the activity of lysine decarboxylase CadA was measured with BP assay.

The process of BP assay was briefly described as follows:

First, the bacterial mass was quantified to $OD_{600}$=5, and then high-pressure disruption was performed to obtain a soluble protein sample containing lysine decarboxylase. The amount of diaminopentane produced was increased by the catalytic reaction of lysine decarboxylase. BP coloring agent can be detected at a wavelength of 595 nm. The reaction conditions listed in Table 1 below were used to measure the activity of lysine decarboxylase. The enzyme activity can be calculated by conversion between the wavelength difference of 595 nm ($\Delta\ OD_{595}$) and the calibration curve of diaminopentane quantified by HPLC.

TABLE 1

Reaction conditions of the assay for measuring the activity of lysine decarboxylase

| Item | Concentration |
|---|---|
| Lysine | 40 mM |
| Pyridoxal-5'-phosphate | 0.2 mM |
| BP coloring agent | 1/20 |
| Sample to be tested | 1/20 |
| Sodium acetate buffer, pH = 6 | |
| Total volume | 500 µL |

Figure 5:
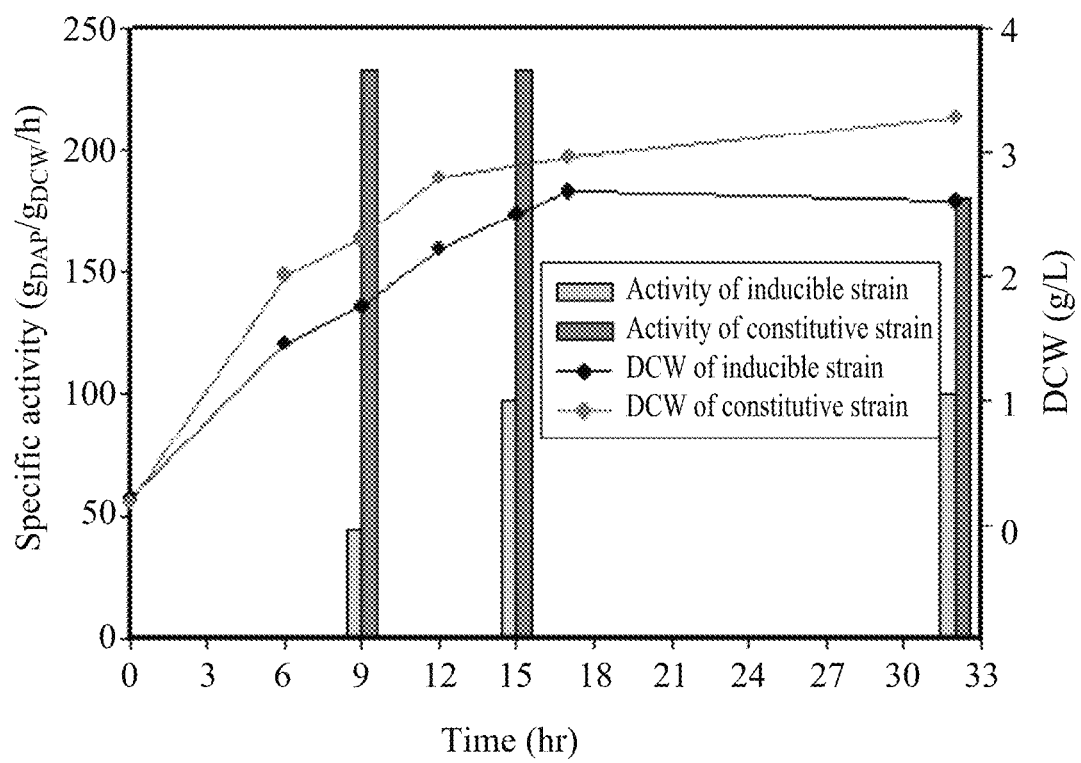
FIG. 5 shows the growth and activity of the constitutive strain and the inducible strain within 30 hours. The constitutive strain is JCadA/W3110 and the inducible strain is *E. coli* T7cadA/BL21 (DE3). Hour 0 is the starting point for inducing *E. coli* BL21 (DE3)-T7cadA with IPTG. DCW: dry cell weight.

As shown in FIG. 5, an inducer was not needed to be added for producing CadA during culture of JCadA/W3110, such that the biomass of JCadA/W3110 was higher than that of the inducible strain at the same time. As to the activity of CadA measured by the BP assay, the results showed that JCadA/W3110, after 30 hours of fermentation, still retained CadA activity above 150 $g_{DAP}/g_{DCW}/h$ (i.e., specific activity), which was even 2 times higher than that of the inducible strain.

Example 6: Plasmid Stability Test

In order to test the stability of plasmids, the transformed strain JCadA/W3110 was subcultured. For the subculture, the strain stocked at −80° C. was inoculated into the medium. After 12 hours of culture, the strain was diluted and coated on the plate medium for activation, indicating as generation 0. Next, a single colony was selected from this activated plate medium and inoculated into the medium; after 12 hours of culture, the strain was diluted and coated on the plate medium, indicating as generation 1. After that, a single colony was selected from the generation 0 plate medium and inoculated into the medium every 7 days for 1 month.

The cells cultured for 12 hours were washed twice with sterilized water, concentrated to a certain OD value, and then heated in a 100° C. water bath for 10 minutes to lyse the cells. After centrifuging at the highest speed for 10 minutes, the cell pellet and substances dissolved from cells were separated. The plasmid copy number was determined by qPCR (quantitative PCR).

Figure 6A:
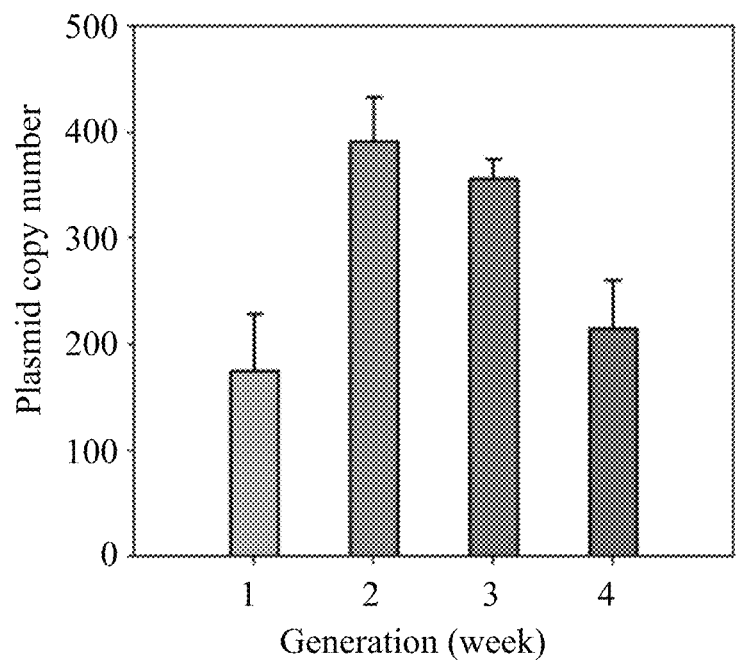
FIGS. 6A and 6B respectively show the plasmid copy number and the protein expression (indicated by arrows) of different generations of transformed strain JCadA/W3110 cultured for 12 hours. The unit of molecular weight marker is kDa.
Figure 6B:
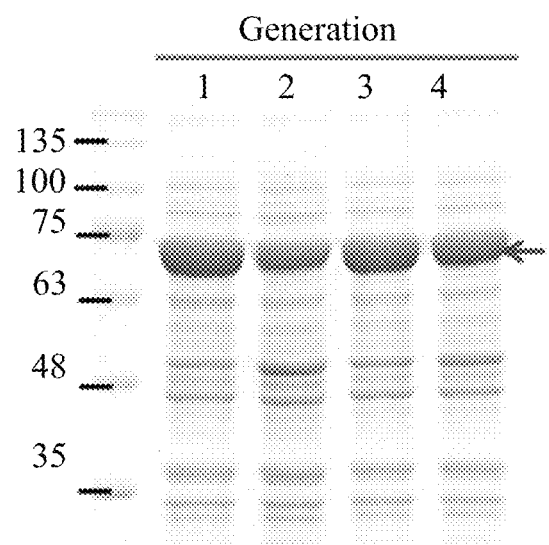

FIG. 6A shows that the colonies activated for 2 weeks can reach the maximum copy number. After 2 weeks, the copy number showed a downward trend. After 1 month of activation, the copy number remained slightly higher than the initial copy number. In addition, FIG. 6B and Table 2 below showed that the protein expression after 2 weeks of activation had a downward trend. From these results, it can be seen that although the copy number of this plasmid has decreased, it can still maintain stable performance.

TABLE 2

Quantitative analysis of protein performance

| Time (days) | Relative amount |
|---|---|
| 0 | 1.00 |
| 7 | 0.32 |
| 14 | 0.43 |
| 28 | 0.77 |

In addition, the transformed strain JCadA/W3110 was cultured in a medium supplemented with antibiotics, and subjected to the stability test under different resistance concentrations. For the resistance culture, the strain stocked at −80° C. was inoculated into the medium as a pre-culture, and then 1% of the pre-culture liquid was inoculated into a 4 mL culture tube. Different concentrations (0, 5, 10 and 25 ppm) of chloramphenicol were added in sequence. The mixtures were incubated in an incubator at 37° C. for 12 hours, and 1 to 2 mL of bacterial solutions were collected for analysis.

Figure 6C:
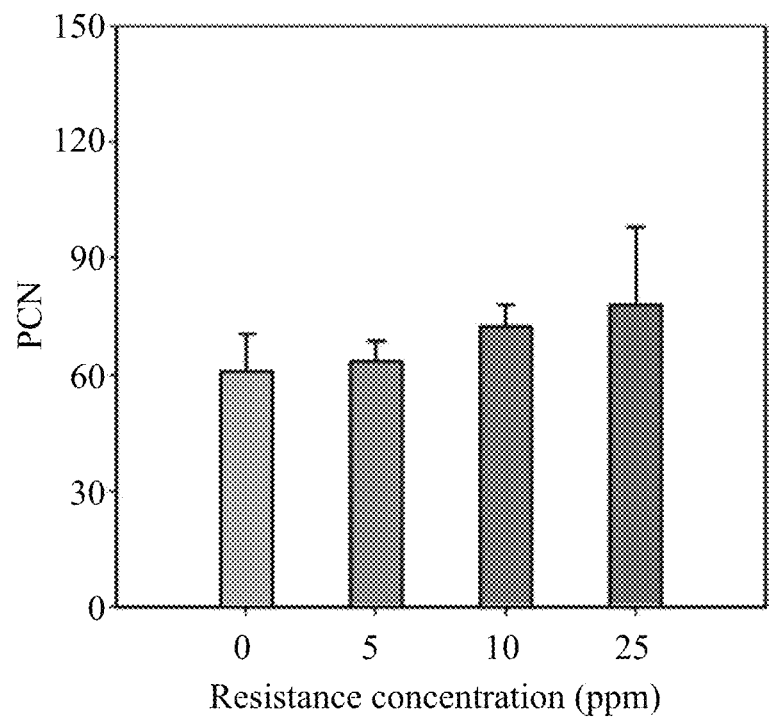
FIGS. 6C and 6D show the plasmid copy number and the protein expression of the transformed strain JCadA/W3110 cultured in different resistance environments for 12 hours, respectively. PCN: plasma copy number.
Figure 6D:
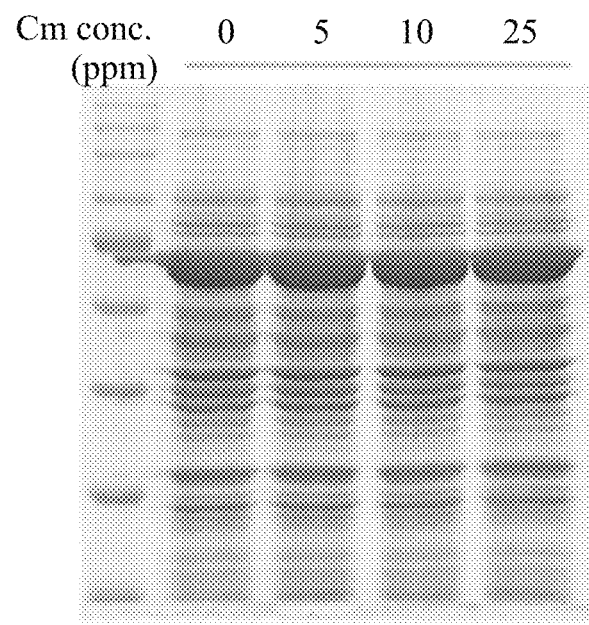

As shown in FIGS. 6C and 6D and Table 3 below, the strains grown at different chloramphenicol concentrations maintained a certain plasmid copy number. The protein expression levels were also maintained, even under the environment without resistance. It thus can be seen that the plasmid can be stably present in the JCadA/W3110 strain.

TABLE 3

Quantitative analysis of protein performance

| Concentration (ppm) | Relative amount |
|---|---|
| 0 | 1.00 |
| 5 | 1.11 |
| 10 | 1.38 |
| 25 | 2.16 |

Example 7: Comparison of Scale-Up Production

In this example, the whole-cell biocatalyst JCadA/W3110 was produced under three culture strategies, i.e., an Erlenmeyer flask, a fermentation tank and a high-density fermentation tank, and the bacterial number and activity were analyzed. The number of bacteria was represented as OD value, which was measured with a spectrophotometer at a wavelength of 600 nm, and the activity of lysine decarboxylase was measured by BP assay. The composition and culture conditions of the medium were shown in Tables 4 and 5 below.

TABLE 4

Medium composition for test

| Medium composition | g/L |
|---|---|
| Glucose | 20 |
| $(NH_4)_2HPO_4$ | 3 |
| $KH_2PO_4$ | 7 |
| Citric acid | 0.8 |
| $MgSO_4 \cdot 7H_2O$ | 1 |
| Yeast extract | 2 |
| Chloramphenicol | 0.025 |
| Trace metal solution | |
| $FeSO_4 \cdot 7H_2O$ | 0.03 |
| $ZnSO_4 \cdot 7H_2O$ | 0.00675 |
| $CuSO_4 \cdot 5H_2O$ | 0.003 |
| $MnSO_4 \cdot 5H_2O$ | 0.0015 |
| $Na_2B_4O_7 \cdot 10H_2O$ | 0.00069 |
| $CaCl_2 \cdot 2H_2O$ | 0.00405 |
| $(NH_4)_6Mo_7O_{24} \cdot 4H_2O$ | 0.0003 |

TABLE 5

Culture conditions

| | Erlenmeyer flask culture | Fermentation tank culture | High-density fermentation tank culture |
|---|---|---|---|
| Container | 250 mL Erlenmeyer Erlenmeyer flask (SCHOTT DURAN, Germany) | 5 L stirred fermentation tank (FB-6S, FIRSTEK, Taiwan) | 5 L stirred fermentation tank (FB-6S, FIRSTEK, Taiwan) |
| Action volume | 50 mL | 3 L | 3 L |
| Inoculation liquid volume ratio | 1:100 | 1:100 | 1:100 |
| pH | No pH control | pH 6.8 | pH 6.8 |
| Dissolved Oxygen (DO) | — | 3 L/min | 3 L/min |
| Temperature | 32° C. | 32° C. | 32° C. |
| Rotation speed | 100 rpm | 100 to 1000 rpm | 100 to 1000 rpm |
| Feed composition | | | Glucose: 418 g/L<br>$MgSO_4 \cdot 7H_2O$: 15 g/L<br>Yeast extract: 50 g/L<br>Chloramphenicol: 0.025 g/L |
| Feed flow rate | | | 0.5 to 1 mL/min |

Figure 7:
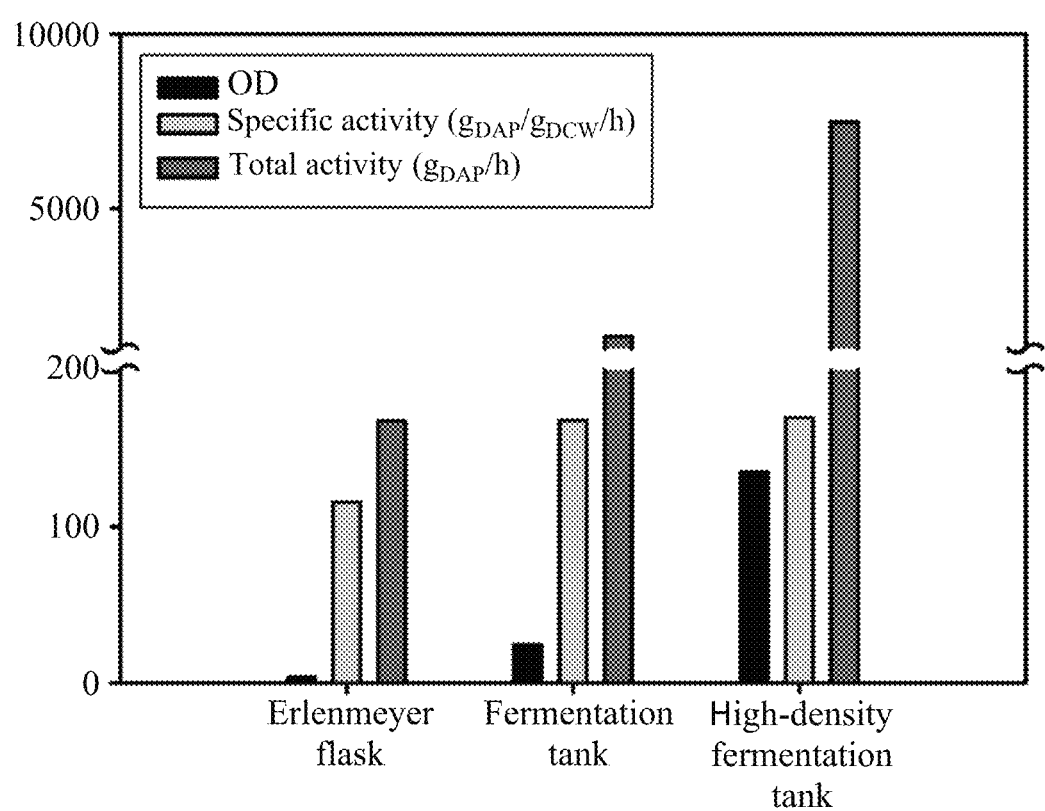
FIG. 7 shows the yield and activity of whole-cell biocatalysts produced by different culture methods.

FIG. 7 showed the yield and activity status of whole-cell biocatalysts produced by the three culture strategies. The quantitative data were also shown in Table 6 below. From these results, it can be seen that, compared with Erlenmeyer flasks and fermentation tanks, culture using high-density fermentation tanks not only increases the amount of bacteria, but also increases the activity per unit of bacteria. Specifically, the use of high-density fermentation can largely increase the amount of bacteria, and produce 30 g/L of lysine decarboxylase with an activity of 170 U/mg/hour, which is useful in preparation of 1,5-diaminopentane whole-cell biocatalyst with high lysine decarboxylase activity.

TABLE 6

Yield of whole-cell biocatalyst produced by different culture methods

| | Erlenmeyer flask | Fermentation tank | High-density fermentation tank |
|---|---|---|---|
| $OD_{600}$ | 4.35 | 24.4 | 134 |
| Specific activity ($g_{DAP}/g_{DCW}/h$) | 116 | 167 | 169 |
| Total activity ($g_{DAP}/h$) | 167 | 1345 | 7473 |

Example 8: Test for Degradation Rate of Activity after Cryopreservation

The whole-cell biocatalyst JCadA/W3110 produced by the fermentation tank was stoked at −80° C. and taken out for culture on Day 20 and Day 130, and the activity state thereof was tested. When thawing, the bacterial mass was quantified with OD value and subjected to disruption, and the activity thereof was measured by BP assay.

Figure 8:
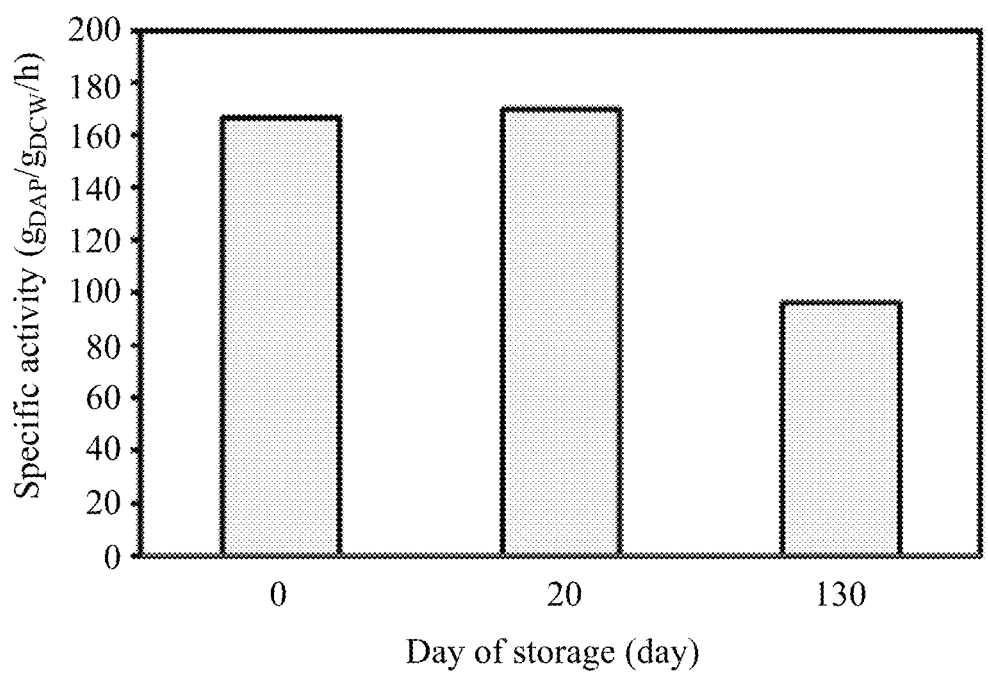
FIG. 8 shows the days and activity of whole-cell biocatalyst cryopreservation at −80° C.

FIG. 8 showed that after 20 days of cryopreservation, JCadA/W3110 still had the same CadA activity as that before the cryopreservation. Furthermore, after 130 days of cryopreservation, it still had about half of the enzyme activity, and contained 95% of the remaining activity related to the inducible strain. It can be seen that the lysine decarboxylase expressed by W3110 using the non-inducible expression system does have the effects of high protein expression, high enzyme activity and slow degradation rate.

The above-mentioned embodiments are only illustrative and not intended to limit the present disclosure. Those skilled in the art can modify and change the above embodiments without departing from the scope of the present disclosure. Therefore, the scope of protection of the rights of the present disclosure is defined by the attached claims. As long as it does not affect the effects and implementation purposes of the present disclosure, it should be encompassed in the technical content of this disclosure.

REFERENCES

[1] Z. G. Qian, X. X. Xia, S. Y. Lee (2011) Metabolic engineering of *Escherichia coli* for the production of cadaverine: a five carbon diamine. Biotechnology and Bioengineering, 108(1), 93-103.

[2] D. H. Kwak, H. G. Lim, J. Yang, S. W. Seo, G. Y. Jung (2017) Synthetic redesign of *Escherichia coli* for cadaverine production from galactose. Biotechnology for Biofuels, 10(1), 20.

[3] J. Wang, X. Lu, H. Ying, W. Ma, S. Xu, X. Wang, K. Chen, P. Ouyang (2018) A novel process for cadaverine bio-production using a consortium of two engineered *Escherichia coli*. Frontiers in Microbiology, 9, 1312.

[4] W. C. Ma, W. J. Cao, H. Zhang, K. Q. Chen, Y. Li, P. K. Ouyang (2015) Enhanced cadaverine production from L-lysine using recombinant *Escherichia coli* co-overexpressing CadA and CadB. Biotechnol. Lett., 37, 799-806.

[5] H. J. Kim, Y. H. Kim, J. H. Shin, S. K. Bhatia, G. Sathiyanarayanan, H. M. Seo, K. Y. Choi, Y. H. Yang, K. Park (2015) Optimization of direct lysine decarboxylase biotransformation for cadaverine production with whole-cell biocatalysts at high lysine concentration, J. Microbiol. Biotechnol., 25, 1108-1113.

[6] W. C. Ma, K. Q. Chen, Y. Li, N. Hao, X. Wang, P. K. Ouyang (2017) Advances in cadaverine bacterial production and its applications, Engineering, 3, 308-317.

---

What is claimed is:

1. An expression vector, comprising a nucleotide sequence for encoding lysine decarboxylase CadA and a sequence of a constitutive promoter for regulating expression of the nucleotide sequence, wherein the nucleotide sequence for encoding lysine decarboxylase CadA is a sequence having at least 98% identity to SEQ ID NO: 1 and the constitutive promoter is one of J series constitutive promoters.

2. The expression vector of claim 1, wherein the nucleotide sequence for encoding lysine decarboxylase CadA is SEQ ID NO: 1.

3. The expression vector of claim 1, wherein the constitutive promoter is J23100, J23109 or J23114.

4. A recombinant microorganism for producing 1,5-diaminopentane, comprising the expression vector of claim 1.

5. The recombinant microorganism of claim 4, which is genus Escherichia, Klebsiella, Erwinia, Serratia, Providencia, Corynebacterium or Brevibacterium.

6. The recombinant microorganism of claim 4, which is recombinant Escherichia coli strain K-12 W3110.

7. The recombinant microorganism of claim 4, which is Escherichia coli W3110-JcadA deposited at Leibniz Institute DSMZ-German Collection of Microorganisms and Cell Cultures under DSMZ Accession No. DSM 33576.

8. A method for producing 1,5-diaminopentane, comprising:
mixing the recombinant microorganism of claim 4 with lysine in a solution to convert the lysine to the 1,5-diaminopentane; and
recovering the 1,5-diaminopentane from the solution.

9. The method of claim 8, further comprising culturing the recombinant microorganism by high-density fermentation before being mixed with the lysine in the solution.

10. The method of claim 8, further comprising adding a cofactor to the solution.

11. The method of claim 10, wherein the cofactor is pyridoxal-5'-phosphate.

* * * * *

SEQUENCE LISTING

```
<160> NUMBER OF SEQ ID NOS: 6

<210> SEQ ID NO 1
<211> LENGTH: 1932
<212> TYPE: DNA
<213> ORGANISM: Escherichia coli

<400> SEQUENCE: 1
atgaacgaga acctgccgtt gtacgcgttc gctaatacgt attccactct cgatgtaagc      60
ctgaatgacc tgcgtttaca gattagcttc tttgaatatg cgctgggtgc tgctgaagat     120
attgctaata agatcaagca gaccactgac gaatatatca acactattct gcctccgctg     180
actaaagcac tgtttaaata tgttcgtgaa ggtaaatata ctttctgtac tcctggtcac     240
atgggcggta ctgcattcca gaaaagcccg gtaggtagcc tgttctatga tttctttggt     300
ccgaatacca tgaaatctga tatttccatt tcagtatctg aactgggttc tctgctggat     360
cacagtggtc cacacaaaga agcagaacag tatatcgctc gcgtctttaa cgcagaccgc     420
agctacatgg tgaccaacgg tacttccact gcgaacaaaa ttgttggtat gtactctgct     480
ccagcaggcg gcaccattct gattgaccgt aactgccaca atcgctgac ccacctgatg     540 atgatgagcg atgttacgcc aatctatttc cgcccgaccc gtaacgctta cggtattctt     600
ggtggtatcc cacagagtga attccagcac gctaccattg ctaagcgcgt gaaagaaaca     660
ccaaacgcaa cctggccggt acatgctgta attaccaact ctacctatga tggtctgctg     720
tacaacaccg acttcatcaa gaaaacactg gatgtgaaat ccatccactt tgactccgcg     780
tgggtgcctt acaccaactt ctcaccgatt tacgaaggta atgcggtat gagcggtggc     840 cgtgtagaag ggaaagtgat ttacgaaacc cagtccactc acaaactgct ggcggcgttc     900
tctcaggctt ccatgatcca cgttaaaggt gacgtaaacg aagaaaacctt taacgaagcc     960 tacatgatgc acaccaccac ttctccgcac tacggtatcg tggcgtccac tgaaaccgct    1020
```

```
gcggcgatga tgaaaggcaa tgcaggtaag cgtctgatta acggttctat tgaacgtgcg   1080
atcaaattcc gtaaagagat caaacgtctg agaacggaat ctgatggctg gttctttgat   1140
gtatggcagc cggatcatat cgatacgact gaatgctggc cgctgcgtcc tgacagcacc   1200
tggcacggct tcaaaaacat cgataacgag cacatgtatc ttgacccgat caaagtcacc   1260
ctgctgactc cggggatgga aaagacggc accatgagcg actttggtat tccggccagc   1320
atcgtggcga ataccctcga cgaacatggc atcgttgttg agaaaaccgg tccgtataac   1380
ctgctgttcc tgttcagcat cggtatcgat aagaccaaag cactgagcct gctgcgtgct   1440
ctgactgact ttaaacgtgc gttcgacctg aacctgcgtg tgaaaaacat gctgccgtct   1500
ctgtatcgtg aagatcctga attctatgaa acatgcgta ttcaggaact ggctcagaat   1560
atccacaaac tgattgttca ccacaatctg ccggatctga tgtatcgcgc atttgaagtg   1620
ctgccgacga tggtaatgac tccgtatgct gcattccaga aagagctgca cggtatgacc   1680
ggagaagttt acctcgacga aatggtaggt cgtattaacg ccaatatgat ccttccgtac   1740
ccgccgggag ttcctctggt aatgccgggt gaaatgatca ccgaagaaag ccgtccggtt   1800
ctggagttcc tgcagatgct gtgtgaaatc ggcgctcact atccgggctt tgaaaccgat   1860
attcacggtg cataccgtca ggctgatggc cgctataccg ttaaggtatt gaagaagaa    1920 agcaaaaaat ga                                                        1932
```

<210> SEQ ID NO 2
<211> LENGTH: 715
<212> TYPE: PRT
<213> ORGANISM: Escherichia coli

<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205
```

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
                275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
                595                 600                 605

Ala Phe Glu Val Leu Pro Thr Met Val Met Thr Pro Tyr Ala Ala Phe
610                 615                 620

Gln Lys Glu Leu His Gly Met Thr Glu Glu Val Tyr Leu Asp Glu Met

```
                    625                 630                 635                 640
Val Gly Arg Ile Asn Ala Asn Met Ile Leu Pro Tyr Pro Pro Gly Val
                            645                 650                 655

Pro Leu Val Met Pro Gly Glu Met Ile Thr Glu Ser Arg Pro Val
                660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
        690                 695                 700

Thr Val Lys Val Leu Lys Glu Glu Ser Lys Lys
705                 710                 715

<210> SEQ ID NO 3
<211> LENGTH: 35
<212> TYPE: DNA
<213> ORGANISM: Artificial Sequence
<220> FEATURE:
<223> OTHER INFORMATION: promoter J23100

<400> SEQUENCE: 3
ttgacggcta gctcagtcct aggtacagtg ctagc                              35

<210> SEQ ID NO 4
<211> LENGTH: 4239
<212> TYPE: DNA
<213> ORGANISM: Artificial Sequence
<220> FEATURE:
<223> OTHER INFORMATION: pSU-J23100-CadA

<400> SEQUENCE: 4
ttgacggcta gctcagtcct aggtacagtg ctagcggatc caaagaggag aaaaagctta    60
tgaacgttat tgcaatattg aatcacatgg gggtttattt taaagaagaa cccatccgtg   120
aacttcatcg cgcgcttgaa cgtctgaact tccagattgt ttacccgaac gaccgtgacg   180
acttattaaa actgatcgaa acaatgcgc gtctgtgcgg cgttattttt gactgggata   240
aatataatct cgagctgtgc gaagaaatta gcaaaatgaa cgagaacctg ccgttgtacg   300
cgttcgctaa tacgtattcc actctcgatg taagcctgaa tgacctgcgt ttacagatta   360
gcttctttga atatgcgctg gtgctgctg aagatattgc taataagatc aagcagacca   420
ctgacgaata tatcaacact attctgcctc cgctgactaa agcactgttt aaatatgttc   480
gtgaaggtaa atatactttc tgtactcctg gtcacatggg cggtactgca ttccagaaaa   540
gcccggtagg tagcctgttc tatgatttct ttggtccgaa taccatgaaa tctgatattt   600
ccatttcagt atctgaactg ggttctctgc tggatcacag tggtccacac aaagaagcag   660
aacagtatat cgctcgcgtc tttaacgcag accgcagcta catggtgacc aacggtactt   720
ccactgcgaa caaaattgtt ggtatgtact ctgctccagc aggcggcacc attctgattg   780
accgtaactg ccacaaatcg ctgacccacc tgatgatgat gagcgatgtt acgccaatct   840
atttccgccc gacccgtaac gcttacggta ttcttggtgg tatcccacag agtgaattcc   900
agcacgctac cattgctaag cgcgtgaaag aaacaccaaa cgcaacctgg ccggtacatg   960
ctgtaattac caactctacc tatgatggtc tgctgtacaa caccgacttc atcaagaaaa  1020
cactggatgt gaaatccatc cactttgact ccgcgtgggt gccttacacc aacttctcac  1080
cgatttacga aggtaaatgc ggtatgagcg gtggccgtgt agaagggaaa gtgatttacg  1140
aaacccagtc cactcacaaa ctgctggcgg cgttctctca ggcttccatg atccacgtta  1200
```

-continued

```
aaggtgacgt aaacgaagaa acctttaacg aagcctacat gatgcacacc accacttctc    1260
cgcactacgg tatcgtggcg tccactgaaa ccgctgcggc gatgatgaaa ggcaatgcag    1320
gtaagcgtct gattaacggt tctattgaac gtgcgatcaa attccgtaaa gagatcaaac    1380
gtctgagaac ggaatctgat ggctggttct ttgatgtatg cagccggat catatcgata     1440 cgactgaatg ctggccgctg cgtcctgaca gcacctggca cggcttcaaa acatcgata    1500 acgagcacat gtatcttgac ccgatcaaag tcaccctgct gactccgggg atggaaaaag    1560
acggcaccat gagcgacttt ggtattccgg ccagcatcgt ggcgaaatac ctcgacgaac    1620
atggcatcgt tgttgagaaa accggtccgt ataacctgct gttcctgttc agcatcggta    1680
tcgataagac caaagcactg agcctgctgc gtgctctgac tgactttaaa cgtgcgttcg    1740
acctgaacct gcgtgtgaaa acatgctgc cgtctctgta tcgtgaagat cctgaattct    1800
atgaaaacat gcgtattcag gaactggctc agaatatcca caaactgatt gttcaccaca    1860
atctgccgga tctgatgtat cgcgcatttg aagtgctgcc gacgatggta atgactccgt    1920
atgctgcatt ccagaaagag ctgcacggta tgaccggaga agtttacctc gacgaaatgg    1980
taggtcgtat taacgccaat atgatccttc cgtacccgcc gggagttcct ctggtaatgc    2040
cgggtgaaat gatcaccgaa gaaagccgtc cggttctgga gttcctgcag atgctgtgtg    2100
aaatcggcgc tcactatccg ggcttttgaaa ccgatattca cggtgcatac cgtcaggctg    2160
atggccgcta taccgttaag gtattgaaag aagaaagcaa aaaatgaaga tctcattaat    2220
gaatcggcca acgcgcgggg agaggcggtt tgcgtattgg gcgctcttcc gcttcctcgc    2280
tcactgactc gctgcgctcg gtcgttcggc tgcggcgagc ggtatcagct cactcaaagg    2340
cggtaatacg gttatccaca gaatcagggg ataacgcagg aaagaacatg tgagcaaaag    2400
gccagcaaaa ggccaggaac cgtaaaaagg ccgcgttgct ggcgtttttc cataggctcc    2460
gcccccctga cgagcatcac aaaaatcgac gctcaagtca gaggtggcga aacccgacag    2520
gactataaag ataccaggcg tttccccctg gaagctccct cgtgcgctct cctgttccga    2580
ccctgccgct taccggatac ctgtccgcct ttctcccttc gggaagcgtg gcgctttctc    2640
atagctcacg ctgtaggtat ctcagttcgg tgtaggtcgt tcgctccaag ctgggctgtg    2700
tgcacgaacc ccccgttcag cccgaccgct gcgccttatc cggtaactat cgtcttgagt    2760
ccaacccggt aagacacgac ttatcgccac tggcagcagc cactggtaac aggattagca    2820
gagcgaggta tgtaggcggt gctacagagt tcttgaagtg gtggcctaac tacggctaca    2880
ctagaagaac agtatttggt atctgcgctc tgctgaagcc agttaccttc ggaaaaagag    2940
ttggtagctc ttgatccggc aaacaaacca ccgctggtag cggtggtttt tttgtttgca    3000
agcagcagat tacgcgcaga aaaaaaggat ctcaagaaga tccttttgatc ttttctacgg    3060 ggtctgacgc tcagtggaac gaaaactcac gttaagggat tttggtcatg agattatcaa    3120
aaaggatctt cacctagatc ctttttaaatt aaaaatgaag ttttaaatca atctaaagta    3180
tatatgagta aacttggtct gacagttacc aatgcttaat cagtgaggca cctatctcag    3240
cgatctgtct atttcgttca tccatagttg cctgactccc cgtcgtgtag ataactacga    3300
tacgggaggg cttaccatct gtcgacaaat tacgccccgc cctgccactc atcgcagtac    3360
tgttgtaatt cattaagcat tctgccgaca tggaagccat cacaaacggc atgatgaacc    3420
tgaatcgcca gcggcatcag caccttgtcg ccttgcgtat aatatttgcc catggtgaaa    3480
acgggggcga gaagttgtc catattggcc acgtttaaat caaaactggt gaaactcacc    3540
cagggattgg ctgagacgaa aaacatattc tcaataaacc ctttagggaa ataggccagg    3600
```

```
ttttcaccgt aacacgccac atcttgcgaa tatatgtgta gaaactgccg gaaatcgtcg    3660
tggtattcac tccagagcga tgaaaacgtt tcagtttgct catggaaaac ggtgtaacaa    3720
gggtgaacac tatcccatat caccagctca ccgtctttca ttgccatacg aaattccgga    3780
tgagcattca tcaggcgggc aagaatgtga ataaaggccg gataaaactt gtgcttattt    3840
ttctttacgg tctttaaaaa ggccgtaata tccagctgaa cggtctggtt ataggtacat    3900
tgagcaactg actgaaatgc ctcaaaatgt tctttacgat gccattggga tatatcaacg    3960
gtggtatatc cagtgatttt tttctccatt ttagcttcct tagctcctga aaatctcgat    4020
aactcaaaaa atacgcccgg tagtgatctt atttcattat ggtgaaagtt ggaacctctt    4080
acgtgcccga tcaactcgag tgccacctga cgtctaagaa accattatta tcatgacatt    4140
aacctataaa aataggcgta tcacgaggca gaatttcaga taaaaaaaat ccttagcttt    4200
cgctaaggat gatttctgga attcgcggcc gcttctaga                          4239

<210> SEQ ID NO 5
<211> LENGTH: 35
<212> TYPE: DNA
<213> ORGANISM: Artificial Sequence
<220> FEATURE:
<223> OTHER INFORMATION: HindIII-CadA-F

<400> SEQUENCE: 5
gcaagcttat gaacgttatt gcaatattga atcac                              35

<210> SEQ ID NO 6
<211> LENGTH: 53
<212> TYPE: DNA
<213> ORGANISM: Artificial Sequence
<220> FEATURE:
<223> OTHER INFORMATION: BglII-CadA-R

<400> SEQUENCE: 6
gcagatcttc atttttgct ttcttctttc aataccttaa cggtatagcg gcc           53
```